US010119965B2

(12) United States Patent
Gondra Zubieta et al.

(10) Patent No.: US 10,119,965 B2
(45) Date of Patent: Nov. 6, 2018

(54) PORTABLE ENRICHMENT, ALIQUOTING, AND TESTING DEVICE OF MICROORGANISMS AND TOXINS

(75) Inventors: Jose Luis Gondra Zubieta, Zamudio (ES); Paloma Aldamiz-Echebarria Zulueta, Zamudio (ES); Javier Escobal Gonzalo, Zamudio (ES); Miren Garbine Olabarria De Pablo, Zamudio (ES); Armando Cruz Llosa, Zamudio (ES); Jesus Berganza Granda, Zamudio (ES); Brigitte Michele Jacqueline Sauvage, Bilbao (ES)

(73) Assignee: FUNDACION GAIKER, Zamudio (ES)

( * ) Notice: Subject to any disclaimer, the term of this patent is extended or adjusted under 35 U.S.C. 154(b) by 295 days.

(21) Appl. No.: 13/498,983

(22) PCT Filed: Sep. 28, 2010

(86) PCT No.: PCT/EP2010/064384
§ 371 (c)(1),
(2), (4) Date: Mar. 29, 2012

(87) PCT Pub. No.: WO2011/039198
PCT Pub. Date: Apr. 7, 2011

(65) Prior Publication Data
US 2012/0196317 A1 Aug. 2, 2012

(30) Foreign Application Priority Data
Sep. 29, 2009 (EP) .................................. 09382187

(51) Int. Cl.
*C12Q 1/04* (2006.01)
*G01N 33/543* (2006.01)

(52) U.S. Cl.
CPC ......... *G01N 33/54366* (2013.01); *C12Q 1/04* (2013.01); *Y02A 50/54* (2018.01)

(58) Field of Classification Search
CPC .... G01N 33/54366; C12Q 1/04; Y02A 50/54; A61B 10/0045
(Continued)

(56) References Cited

U.S. PATENT DOCUMENTS 3,563,859 A * 2/1971 Fink ............................ 435/287.1
4,741,437 A * 5/1988 Gorski ....................... A61L 2/28
206/222
(Continued)

FOREIGN PATENT DOCUMENTS

EP 1712614 10/2006
FR 2849861 7/2004
(Continued)

OTHER PUBLICATIONS

PCT Search Report prepared for PCT/EP2010/064384, dated Apr. 28, 2011.

*Primary Examiner* — Michael L Hobbs
*Assistant Examiner* — Liban M Hassan
(74) *Attorney, Agent, or Firm* — Barnes & Thornburg LLP

(57) ABSTRACT

The present invention relates to devices for conducting microorganism or toxin detection. More particularly, the invention relates to portable, pre-packaged devices that are suitable for culturing microorganisms, aliquoting predetermined volumes of testing samples, and conducting microorganism or toxin detection based on immunological reactions using samples of considerable size collected at remote sites away from testing laboratories.

7 Claims, 8 Drawing Sheets

(58) Field of Classification Search
USPC ............... 435/288.2, 29, 287.1, 287.2, 288.3
See application file for complete search history.

(56) References Cited

U.S. PATENT DOCUMENTS

| | | | |
|---|---|---|---|
| 5,393,496 A * | 2/1995 | Seymour .................. 422/413 |
| 5,566,845 A * | 10/1996 | Frank .................... B65D 25/44 |
| | | | 215/208 |
| 5,916,815 A | 6/1999 | Lappe | |
| 6,197,574 B1 * | 3/2001 | Miyamoto et al. ........ 435/287.6 |
| 2002/0046614 A1 * | 4/2002 | Alley ..................... B01L 3/502 |
| | | | 73/864.51 |
| 2004/0132091 A1 * | 7/2004 | Ramsey ............... A61B 10/007 |
| | | | 435/7.1 |
| 2005/0106750 A1 | 5/2005 | Tung et al. | |
| 2006/0088895 A1 | 4/2006 | Wanders et al. | |
| 2006/0148068 A1 | 7/2006 | Noury | |
| 2007/0249040 A1 | 10/2007 | Miyamoto et al. | |
| 2009/0031790 A1 * | 2/2009 | Guo et al. .................. 73/64.56 |
| 2009/0197283 A1 * | 8/2009 | Gold et al. .................. 435/7.9 |

FOREIGN PATENT DOCUMENTS

| | | |
|---|---|---|
| GB | 2127542 | 4/1984 |
| WO | WO1994/028163 | 12/1994 |
| WO | WO1997/003209 | 1/1997 |
| WO | WO1999/002650 | 1/1999 |

\* cited by examiner

SECTION A-A

SECTION A-A

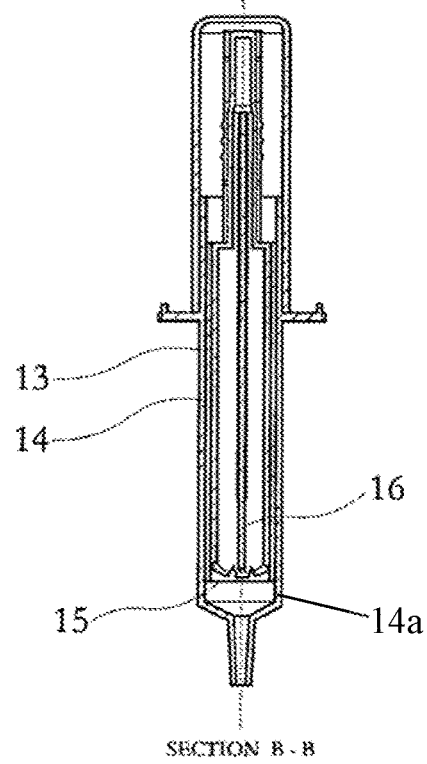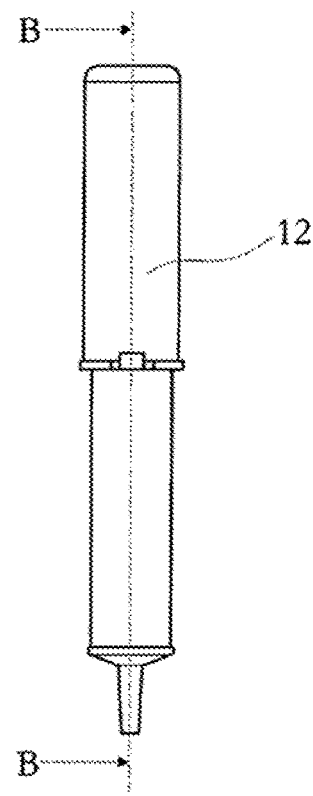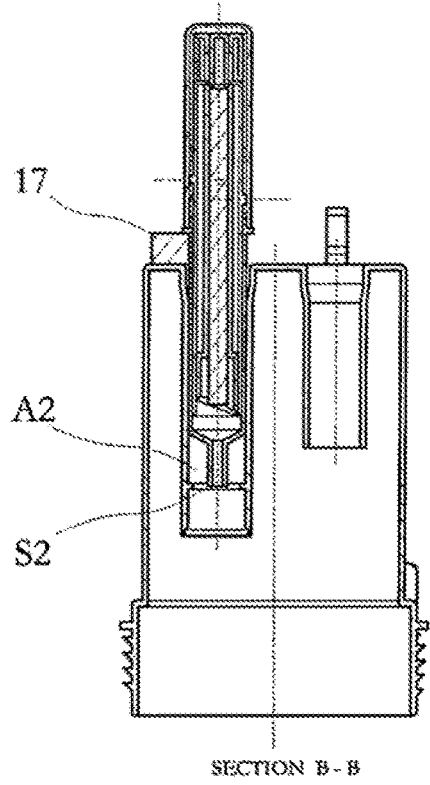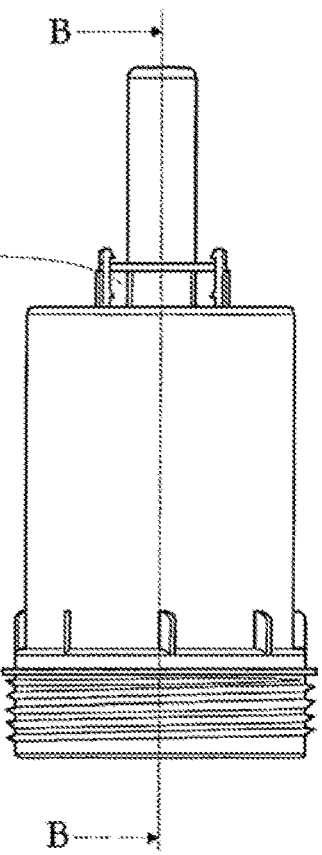
Fig. 7
Fig. 8

SECTION A-A

SECTION A - A

PORTABLE ENRICHMENT, ALIQUOTING, AND TESTING DEVICE OF MICROORGANISMS AND TOXINS

CROSS-REFERENCE TO RELATED APPLICATIONS

This application is a U.S. national counterpart application, filed under 35 U.S.C. § 371, of International Application Ser. No. PCT/EP2010/064384, filed Sep. 28, 2010, which claims priority to European Patent Application Ser. No. 09382187.4, filed Sep. 29, 2009. The disclosures of both applications are hereby incorporated herein by reference in their entirety.

FIELD OF THE INVENTION

The present invention relates to devices for conducting microorganism or toxin detection. More particularly, the invention relates to portable, pre-packaged devices that are suitable for culturing microorganisms, aliquoting pre-determined volumes of testing samples, and conducting microorganism or toxin detection based on immunological reactions using samples of considerable size collected at remote sites away from testing laboratories.

BACKGROUND OF THE INVENTION

Food or environmental contamination may be defined as the presence in food or the environment of harmful, unpalatable, or otherwise objectionable foreign substances, e.g. chemicals, microorganisms or diluents.

Ideal microorganism and toxin detection in the food industry and all industries in general should have at least some of the following characteristics: ability to detect a number of different pathogens at a cost that is affordable; ability to easily incorporate new pathogen tests into regimes to ensure that any emerging pathogens is not overlooked; detection should be simple to perform by untrained personnel; it should require only minimal or no instrumentation and preclude mistakes and poor performance resulting in incorrect interpretation; it should be sensitive enough to detect low levels of pathogens, and yet specific for detection of the pathogenic species of interest.

Most conventional methods for detecting foodborne bacterial pathogens in food and other substances rely on the use of microbiological media to selectively grow and enumerate bacterial species. The methods are sensitive and inexpensive, and provide qualitative as well as quantitative results. Unfortunately for the food industry, where time and costs are issues, the preparation of media and plates, colony counting, and biochemical characterization of the isolated colonies make for a time-consuming and labor-intensive process (de Boer and Beumer 1999).

WO1999002650 (Oxoid Limited) relates to a selective enrichment and detection method of microorganisms that comprises incubating the sample in a pre-enrichment medium, with one or more selective agents to favor growth of the target microorganism arranged for release into the medium after a predetermined time delay. The method presented therein combines pre-enrichment and selective enrichment steps by use of timed release of the selective agent(s).

WO1994028163 (Foss Electric AS) relates to a method for the determination of *Salmonella*, comprising an enrichment step and a determination step. The enrichment procedure involves selective conditions, notably the use of the selective substances tetrathionate and/or novobiocin or an increase in culturing temperature to 39-43° C., favouring the early detection of *Salmonella*.

Devices for analysing samples are known from U.S. Pat. No. 6,197,574 B1 by Miyamoto et al, WO 97/03209 A1 by Charm Sciences. Inc. Et Al., Fr 2 849 861 A1 form Giat Industries S.A., US 2009/197283 A1, from Gold Et A1, EP 1 712 614 A1 form SRL. Inc. Et al, and US 2006/088895 A1 from Wanders et al, almost all of them describing test tubes provided with collector sticks destined to collect a microsample by scratching the surface of an object which could contain biological hazard agents.

From a public health perspective, faster detection times are essential to prevent the spread of infectious diseases or the identification of a continuing source of infection. In situ testing in the potentially contaminated premises is therefore more desirable than shipping samples for later laboratory testing.

Widely employed rapid testing methods include immunoassays and polymerase chain reaction (PCR) based tests. Immunoassays are antibody-based tests that are sensitive diagnostic tools for the in vitro detection of a variety of antigens associated with disease or other physical conditions of clinical significance. PCR-based tests are considered especially attractive due to their relative low cost and potential application in large-scale screening programs by means of automated technologies. However, PCR testing is still a complex technique for application in routine analysis, thereby requiring qualified personnel and specialized laboratory machinery.

It is an object of the present invention to provide a device that allows the detection of food or environmental contamination in situ.

It is an object of the present invention to provide a device that allows the enrichment of macro samples, like a piece of meat, fish, cheese, etc.

It is an object of the present invention to provide a device that allows the detection of contaminating microorganisms and toxins in macro samples, like a piece of meat, fish, cheese, etc.

It is an object of the present invention to provide a device that permits the introduction of a test sample into the device without accidentally contaminating the interior components of the device.

It is an object of the invention to provide a device that allows manipulating in a comfortable, safe and easy way macrosamples of meat or the like.

In the present description macrosample refers to samples that weight a few grams, i.e., samples corresponding to a piece of meat or the like. With this meaning, a sample obtained by scratching a piece of food or by dipping in it a collector stick does not fall in the scope of a macrosample.

It is an object of the present invention to provide a device that allows contaminants detection without accidentally contaminating the surrounding premises. It is an object of the present invention to provide a device for detecting food or environmental contamination that contributes to, complies with, and therefore may be used in a contingency plan for food or environmental contamination.

It is an object of the present invention to provide a device that is easy and simple to be handled by untrained personnel.

It is an object of the present invention to provide a device that enables the extraction of exact or pre-determined aliquots of a mixture of a test sample and culture media by untrained personnel without requiring a control or verification.

It is an object of the present invention to provide a device that allows the extraction of exact or pre-determined aliquots of an enriched and filtered sample in a confined receptacle where its analytes can be further extracted and detected.

It is an object of the present invention to provide a device that integrates 3 processing chambers into one single chamber, i.e. those chambers for filtering an enriched aliquot, for analyte extraction, and for analyte detection.

It is an object of the present invention to provide a device that integrates 3 processing chambers into one single chamber, which is a watertight compartment.

It is an object of the present invention to provide a device that integrates 3 processing chambers into one single chamber, which moreover maintains its autonomy and function during each of the 3 processing steps, i.e. filtering, analyte extraction, and analyte detection.

It is an object of the present invention to provide a device that allows the manipulation of and assaying a test sample with a lateral flow immunochromatography strip by untrained personnel.

It is an object of the present invention to provide a device that avoids disabling lateral flow immunochromatography strips, by incorrect or accidental manipulation.

It is an object of the present invention to provide a device that is industrially manufacturable.

It is an object of the present invention to provide a device that employs injection molds in cost-effective series, thereby facilitating automatic assembly.

It is an object of the present invention to provide a device that is not expensive.

It is an object of the present invention to provide a device that is portable, that allows in situ detection of food or environmental contamination.

It is an object of the present invention to provide a device that is disposable, particularly in non-specialized waste containers or facilities.

It is an object of the present invention to provide a device that allows the circulation and processing of the sample to be finally detected and read, to be used by untrained personnel, and with minimal manipulation.

It is an object of the present invention to provide a device that eliminates the risks of malfunctioning, flaws, or wrong manipulation by the user.

SUMMARY OF THE INVENTION

The aim of the invention is reached with a portable device for detecting biological hazard agents in a sample comprising a container enclosing a first housing filled with a culture medium for biological hazard agents, a second housing for receiving the sample, a lid that can be coupled to the container for closing said second housing, means for (fluid)-communicating the first and the second housing that allows obtaining a sample ready for testing and means for sensing the presence of biological hazard agents in the sample ready for testing, characterised in that the second housing has an inlet surface greater than 10 and it comprises a lateral wall provided with at least one visual indicator corresponding to a predetermined filling volume, such that it is possible to collect in a safe and easy way a macro-sample, to prepare it and detect the presence of biological hazard agents in a safe way.

These features allows to handle and manipulate in a comfortable, fast and easy way a macro-sample, especially to a non-skilled person. Instead of scratching with a collector, the user has to deposit or pour the sample in a housing, which has an inlet surface that prevents form pouring sample out of it. The visual indicator, for example a level mark, indicates the volume to be filled with the sample, thus guarantying that the sample quantity is appropriate for the culture medium volume.

In state of the art devices this is not possible, because the inlet, i.e. the inlet of the tubes, are destined to house a collecting stick, not a macro sample.

Another advantage is that it allow to comply with regulations, that establishes the minimum weight of the samples.

According to a first embodiment, the second housing is in the lid, which more preferably is a plate. Therefore, the user can prepare the sample in an easy way. He can let the plate leaning on a surface, and pour inside the sample. Then, after, he just have to couple the lid to the container.

In state of the art devices, after scratching the sample, the user has to look for the rest of the device and couple it. Moreover, he won't be able to let it upwards on a table, instead he will need a support for guarantying it keeps vertical.

According to another embodiment, the second housing is in the container. Therefore, the same operations as described in relation to the first embodiment have to be carried out, but this time the operation of coupling the lid is done like with any common container, by closing it form the top.

More preferably, the first housing has a volume comprised between 50 and 500 ml, and the second housing has a volume comprised between 5 and 300 ml.

Preferably, the lid and the container comprised two mutually threaded complementary surfaces such that the lid and the container can be coupled by screwing. Another option can be a coupling by pressing with a positive movement.

Advantageously, the device comprises means for prevent uncoupling of the lid when a first determined coupling position has been reached, and therefore, it will be possible to prevent the lid from opening once the culture medium has been mixed with the sample.

More advantageously, the means for (fluid)-communicating the first and the second housing are activated when a second determined position has been reached.

The coupling course the first determined position is reached before the second determined position, such that risk of leakage of the culture medium is prevented.

According to a preferred embodiment, the means for (fluid)-communicating the first and the second housing comprise a seal separating the first and the second housing which can be torn by cutting elements arranged in the lid. In this case, the lid comprises and outer perimeter wall provided with an inner threaded, and an inner perimeter wall provided with cutting elements destined to tear the seal, said second housing being enclosed by said inner perimeter wall.

In another embodiment, the means for (fluid)-communicating the first and the second housing comprise two adjacent mutually rotating walls, one of them enclosing the first housing, the second one enclosing the second housing, said walls being provided with holes arranged in a way such that they coincide when the second determined position is reached.

In yet another embodiment, the means for (fluid)-communicating the first and the second housing comprise a valve that opens automatically when the second determined position is reached.

In another embodiment, the means for (fluid)-communicating the first and the second housing comprises a valve or seal with an opening element that can be activated manually, said opening element being blocked until the second determined position is reached.

The device can comprise inertizing means enclosed in a fourth housing, and more preferably means for preventing the inertizing means to be activated until the second position has been reached. The fourth housing containing the inertizing means can be arranged in the lid.

These inertizing means can be solid, for example a pill arranged in a housing which walls separating it from the sample can be broken by pressing it, that is to say a blister unit (B in FIG. 16). The inertizing means could be liquid and/or chemical and/or biological. They could be in a form of powder, or beads.

The means for sensing the presence of biological hazard agents in the sample comprises an inmunocromatography strip, preferably enclosed in a third housing provided with a transparent surface that allows the strip to be seen from the outside. This means could be chromogenic culture medium.

Finally, the second housing is partially enclosed by a septum that allows the sample to be accessed from the outside.

The invention also relates to a method for detecting biological hazard agents in a sample using a portable device, said portable device comprising a container enclosing a first housing filled with a culture medium for biological hazard agents, a second housing for receiving the sample, a lid that can be coupled to the container for closing said second housing, means for (fluid)-communicating the first and the second housing that allows obtaining a sample ready for testing and means for sensing the presence of biological hazard agents in the sample ready for testing, wherein the second housing has an inlet surface greater than 10 cm2, and preferably lesser than 100 cm2, and it comprises a lateral wall provided with at least one visual indicator corresponding to a predetermined filling volume, said method comprising the steps of:
fill the second housing through the inlet surface with a sample until the visual indicator corresponding to a predetermined filling volume is reached;
close the housing with the lid;
activate the means for (fluid)-communicating the first and the second housing;
after a minimum culture time has elapsed, such that the sample is ready for testing, activate the means for sensing the presence of biological hazard agents in the sample ready for testing
such that it is possible to collect in a safe and easy way a macro-sample, to prepare it and detect the presence of biological hazard agents in a safe way.

Preferable, said method comprises a further step of inertizing the macrosample and the culture medium.

The present invention also relates to a device (1) for assaying microorganisms or toxins comprising:
a container (2) enclosing a volume (3) filled with a culture medium for a microorganism and provided with a first aperture (A1) sealed with a first seal (S1) and a second aperture (A2) sealed with a second seal (S2);
a lid (4) for covering said first aperture (A1), said lid (4) defining a housing (5) for receiving a test sample (TS),
means (6) for mechanically tight coupling the lid (4) to the container (2); and
means (7) for breaking the first seal (S1) of said first aperture (A1) at a determined position (P1) of the coupling course between the lid (4) and the container (2), thus bringing the culture medium into contact with the test sample.

This device (1) according to the present invention is useful as an enricher or aliquoter of test samples.

The present invention further relates to a testing injector device (12) configured for accessing the volume (3) of the device (1) according to any one of claims 1-6 through the second aperture (A2) of the container (2) by perforating the second seal (S2), said injector device (12) comprising a tube (13) and a slidable plunger (14), wherein the plunger comprises a seal (15) at its bottom (14a) and a lateral flow immunochromatography strip (16) inside along the plunger (14).

The present invention additionally relates to an inactivating injector device (22) configured for accessing the volume (3) of the device (1) according to claim 9 through the third aperture (A3) of the container (2) by perforating the third seal (3), said injector device (22) comprising a tube (23) and a slidable plunger (24), wherein the tube comprises a seal (25) at its bottom (23a) and inactivating agent, and the plunger (24) has a sharp end.

The device (1), (12), or (22) according to the present invention are useful as detectors of environmental or food contamination.

DESCRIPTION OF THE FIGURES

FIG. 7 shows a testing injector device (12) comprising a tube (13) and a slidable plunger (14), wherein the plunger comprises a seal (15) at its bottom (14a) and a lateral flow immunochromatography strip (16) inside along the plunger (14).

FIG. 8 shows security means (17) which when released, allow the injector device (12) to be pushed into the second aperture (A2) and perforate seal (S2).

DESCRIPTION OF THE INVENTION

Definitions

Figure 1:
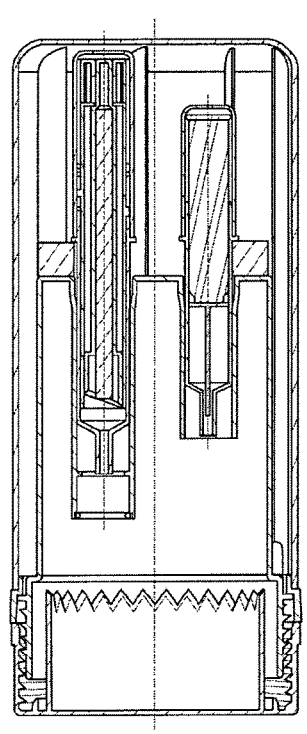
FIG. 1 is a cross-section of the device (1)
Figure 1:
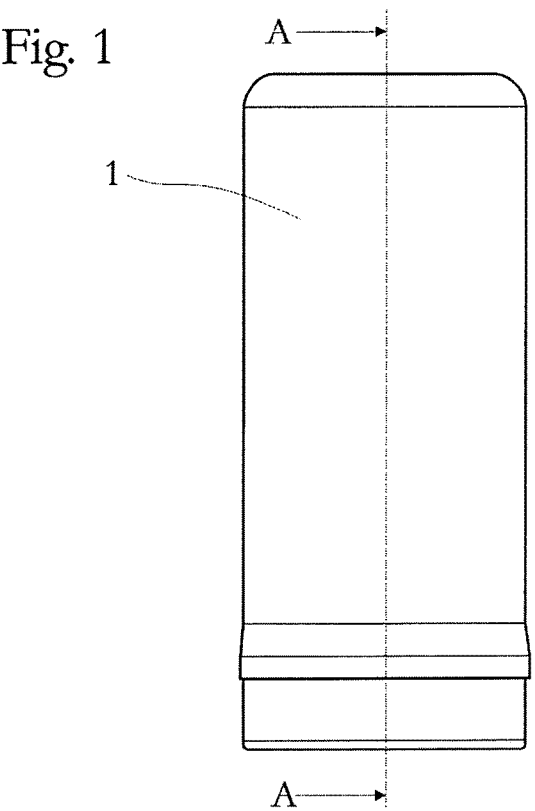
Figure 2:
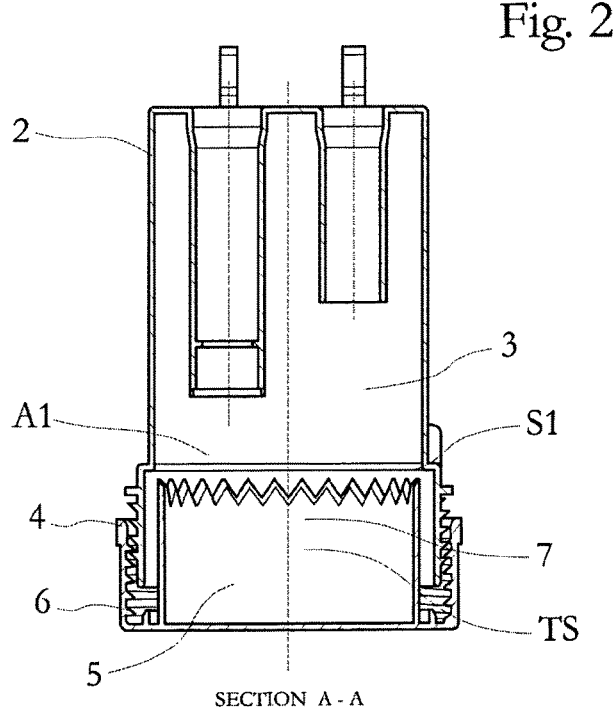
FIG. 2 shows a container (2) enclosing a volume (3) and provided with a first aperture (A1) sealed with a first seal (S1), a lid (4) defining a housing (5) for receiving a test sample (TS), means (6) for mechanically tight coupling the lid (4) to the container (2), means (7) for breaking the first seal (S1).
Figure 2:
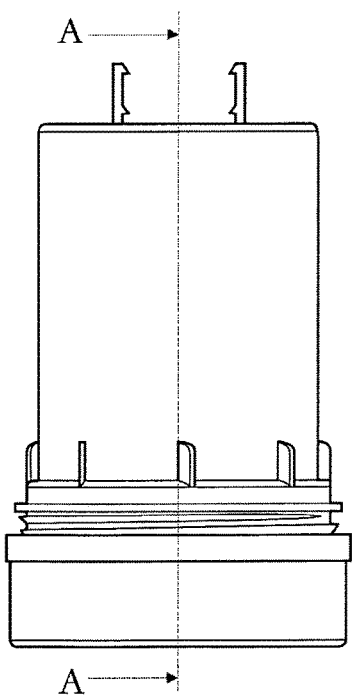

The term "microorganism" refers to an organism that is microscopic, usually too small to be seen by the naked human eye, and includes bacteria, fungi, virus, archaea, and protists; microscopic plants (called green algae); and animals such as plankton and the planarian.

Microorganisms of interest include enteric viruses (hepatitis A virus, rotavirus, astrovirus, enteric adenovirus, hepatitis E virus, *Bovine Spongiform Encephalopathy* (BSE) prions, and the human caliciviruses consisting of the noroviruses like the Norwalk viruses and the Sapporo viruses); parasites such as *Cyclospora, Giardia lamblia*, the beef and pork tapeworms (*Taenia saginata* and *Taenia solium*, respectively), the roundworm that causes trichinosis (*Trichinella spiralis*), the nematodes or roundworms (*Anisakis* spp., *Pseudoterranova* spp., *Eustrongylides* spp. and *Gnathostoma* spp.), cestodes or tapeworms (*Diphyllobothrium* spp.), and trematodes or flukes (*Chlonorchis sinensis, Opisthorchis* spp., *Heterophyes* spp., *Metagonimus* spp., *Nanophyetes salminicola* and *Paragonimus* spp.); molds producing mycotoxins (Species of *Aspergillus, Fusarium, Penicillium*, and *Claviceps*); *Yersinia enterocolitica; Vibrio* species (*Vibrio cholerae Vibrio parahaemolytitucs, Vibrio vulnificus, Vibrio mimicus, Vibrio hollisae, Vibrio fluvialis*, and *Vibrio furnissii*); *Staphylococcus aureus; Campylobacter* spp. (primarily *C. jejuni* subsp. *Jejuni*); *Listeria monocytogenes; Salmonella; Shigella* especies (*S. dysenteriae, S. flexneri, S. boydii*, and *S. sonnei*); *Escherichia coli* O157:H7; *Clostridium botulinum* and *Clostridium perfringens; Bacillus cereus* (*B. anthracia, B. cereus, B. mycoides, B. pseudomycoides, B. thuringiensis* and *B. weihenstephanensis*). Microorganisms of interest of the present invention are those foodborne pathogens.

The term "toxin" refers to specific, characterizable, poisonous chemicals, often proteins, with specific biological properties, including immunogenicity, produced by microbes, higher plants, or animals including men. Toxic substances not produced by living organisms are also comprised in the definition of "toxin".

Examples of toxins include microbial toxins such as enterotoxins, neurotoxins, cereulide, Botulinum neurotoxin, Anthrax toxin, Subtilase cytotoxin, *Pasteurella multocida* toxin, *Vibrio* RTX toxins, *cholera* toxin, *Helicobacter pylori* toxin, *Staphylococcal* toxins, fungal ribotoxins, *Cyanobacteria* toxins, *aflatoxins, ciguatoxin, scombrotoxin, deoxynivalenol, ochratoxin A, fumonisins, ergot alkaloids*, T-2 toxin, zearalenone, and other minor mycotoxins such as cyclopiazonic acid and patulin.

The term "culture medium" refers herein to any liquid or solid preparation made specifically for the growth of microorganisms or other types of cells present in the test sample. The culture medium is usually a selective medium that comprises several antimicrobial agents to suppress the growth of bacteria of no interest. The culture medium includes those nutrients suitable for accelerating the growth of the microorganism of interest. Preservatives may also be added.

Examples of culture medium include, without being limited to, nutrient broths (liquid nutrient medium) or Luria Bertani medium (LB medium or Lysogeny Broth). The type of culture medium generally depends on the microorganism to be enriched or grown and further detected.

The term "seal" refers to a closure that must be broken to be opened. It can be made of any material such as soft or hard plastic, films, as long as it prevents the leakage of liquid, solid, or gas materials, while allowing its break through the use of reasonable force or pressure. Typical seals are those yoghurt seals made of aluminium. Instead, a breakable thin plastic wall may be used.

The term "test sample" refers to that material obtained from sources like biological materials, food, beverages, or the environment including air, water, machinery, industrial surfaces, etc. Biological materials include those obtained from animals, plants, eatable fungi, and may be any tissue sample, body fluid, body fluid precipitate, or lavage specimen. Body fluids include blood, serum, lymph, scrapings, sweat, feces, urine. Such sources are not meant to be exhaustive, but rather exemplary.

The term "mesh" or "mesh filter", also called sieve or filter, refers to a semi-permeable barrier made of connected strands of metal, fiber, or other flexible or ductile material. Mesh includes also a web or net in that it has many attached or woven strands. Any material useful for separating macroscopic pieces of solid sample from the mixture of culture medium and test sample is contemplated in this definition.

The term "extraction medium" refers to an analyte extraction agent. The extraction medium in the testing injector device is optional depending on the microorganism (gram positive or gram negative, i.e., with or without membrane) or toxin to be analyzed. Its function is to liberate the antigenic determinants present in the test sample such that they become accessible for their further detection with the immunochromatography strip. The extraction medium, also called lysis medium, may be in powder, liquid, or gel form. If liquid, the testing injector device preferably comprises a check valve, more preferably located at its tip.

Example of extraction medium include, without being limited to, tensoactives, enzymatic blends, sulphates or other chemical, biochemical reagents that could be suitable for this purpose.

The term "immunochromatography strip" or "lateral flow immunochromatography strip" refers to any chromatographic media (e.g., nitrocellulose, cellulose acetate, paper, nylon, cellulose, glass fiber, polyester, or any other suitable bibulous material) through which a liquid sample, suspected of containing an analyte to be detected, can flow by capillary action, and where detection of the analyte utilizes an antibody or antibody fragment that bind specifically thereto, i.e. detection is performed with an immunoassay. This specific affinity refers to a binding reaction which is determinative of the presence of the analyte in the presence of a heterogeneous population of molecules such as proteins and other biologics (i.e., such as may be found in the culture and test sample mixture). Thus, under designated immunoassay conditions, the specified antibodies bind to a particular analyte and do not bind in a significant amount to other analytes present in the sample.

A "label" is a composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas Red, rhodamine, green fluorescent protein, and the like), radiolabels (e.g., 3H, 25I, 35S, 14C, or 32P), enzymes (e.g., horse radish peroxidase, alkaline phosphatase and others commonly used in an ELISA), and colorimetric labels such as colloidal gold, silver, selenium, or other metals, or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The term "inactivating agent" refers to a substance or composition able to disinfect, sanitize, destroy, eliminate, or inertisize, microorganisms and toxins, particularly those pathogenic, to levels considered safe according to public health ordinance, or that reduce the microbial or toxin population by significant numbers where public health requirements have not been established. Preferably, the inactivating agent is environmentally friendly and has a broad spectrum of antimicrobial activity. Examples of inactivating agent include, without being limited to, oxidizing agents such as hydrogen peroxide, sodium hypochlorite (bleach), chlorine compositions, iodine, ozone; alcohols such as ethanol and isopropanol; aldehydes like glutaraldehyde; phenolics such as phenol, O-phenylphenol, chloroxylenol, or thymol; quaternary ammonium compounds (Quats) such as benzalkonium chloride.

EMBODIMENTS OF THE INVENTION

Figure 16:
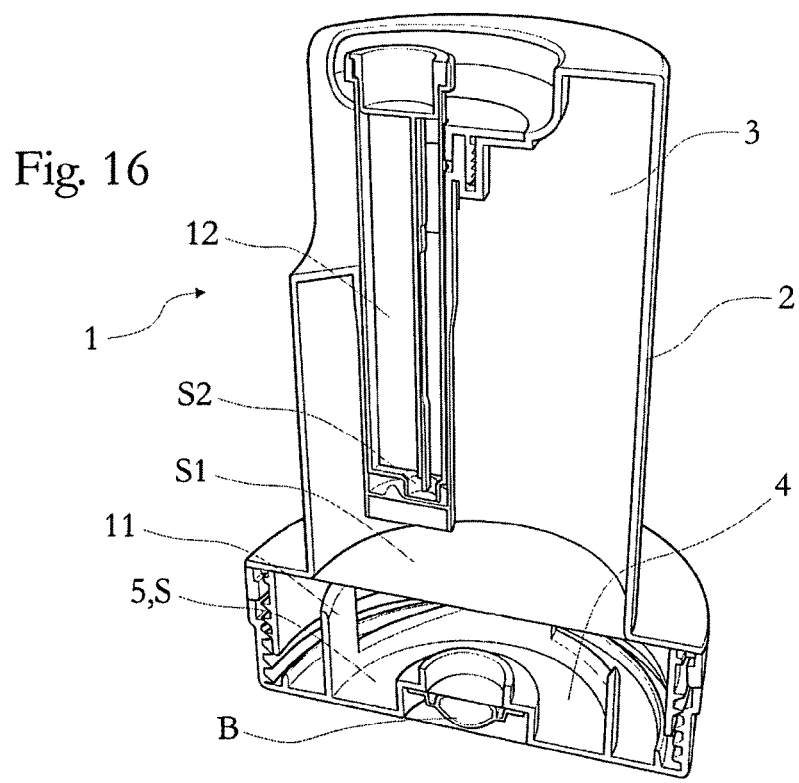
FIG. 16 shows a section of an embodiment provided with a lid/plate, which in turn comprises a blister (B).

As shown in FIG. 16, the applicant claims a portable device (1) for detecting biological hazard agents in a sample (S) comprising a container (2) enclosing a first housing (3) filled with a culture medium for biological hazard agents, a second housing (5) for receiving the sample (S), a lid (4) that can be coupled to the container (2) for closing said second housing (5), means for (fluid)-communicating the first (3) and the second housing (5) that allows obtaining a sample (S) ready for testing and means for sensing the presence of biological hazard agents in the sample (S) ready for testing, wherein the second housing (5) has an inlet surface comprised between 10 and 100 cm2 and it comprises a lateral wall provided with at least one visual indicator corresponding to a predetermined filling volume, such that it is possible to collect in a safe and easy way a macro-sample (S), to prepare it and detect the presence of biological hazard agents in a safe way.

The second housing is in the lid (4), which preferably is a plate. This plate allows to fill it comfortably with the quantity of sample required, thanks to the visual indicator. It allows specially carry out the method claimed.

In another embodiment, not shown, the second housing (3) is in the container (2).

In whatever embodiment, the first housing (3) has a volume comprised between 50 and 500 ml, and the second housing (5) has a volume comprised between 5 and 300 cm3, thus allowing to prepare samples in a way that complies with the regulations mentioned below.

As shown in the figures, he lid and the container comprise two mutually threaded complementary surfaces such that the lid and the container can be coupled by screwing.

The present invention relates also to a device (1) for assaying microorganisms or toxins comprising:

a container (2) enclosing a volume (3) filled with a culture medium for a microorganism and provided with a first aperture (A1) sealed with a first seal (S1) and a second aperture (A2) sealed with a second seal (S2);

a lid (4) for covering said first aperture (A1), said lid (4) defining a housing (5) for receiving a test sample (TS), means (6) for mechanically tight coupling the lid (4) to the container (2); and means (7) for breaking the first seal (S1) of said first aperture (A1) at a determined position (P1) of the coupling course between the lid (4) and the container (2), thus bringing the culture medium into contact with the test sample.

In one embodiment of the present invention, the means (6) for mechanically tight coupling the lid (4) to the container (2) or vice versa, comprise two mutually engaging threaded surfaces on the lid (4) and the container (2), respectively.

In one embodiment of the present invention, the second aperture (A2) is a channel (8).

In one embodiment of the present invention, the second seal (S2) is placed in an intermediate part of the second aperture (A2). In a further embodiment, the second seal (S2) is placed in an intermediate part of the channel (8).

In one embodiment of the present invention, the container (2) is further provided with a mesh (9) on the volume side with respect to said second seal (S2).

Figure 3:
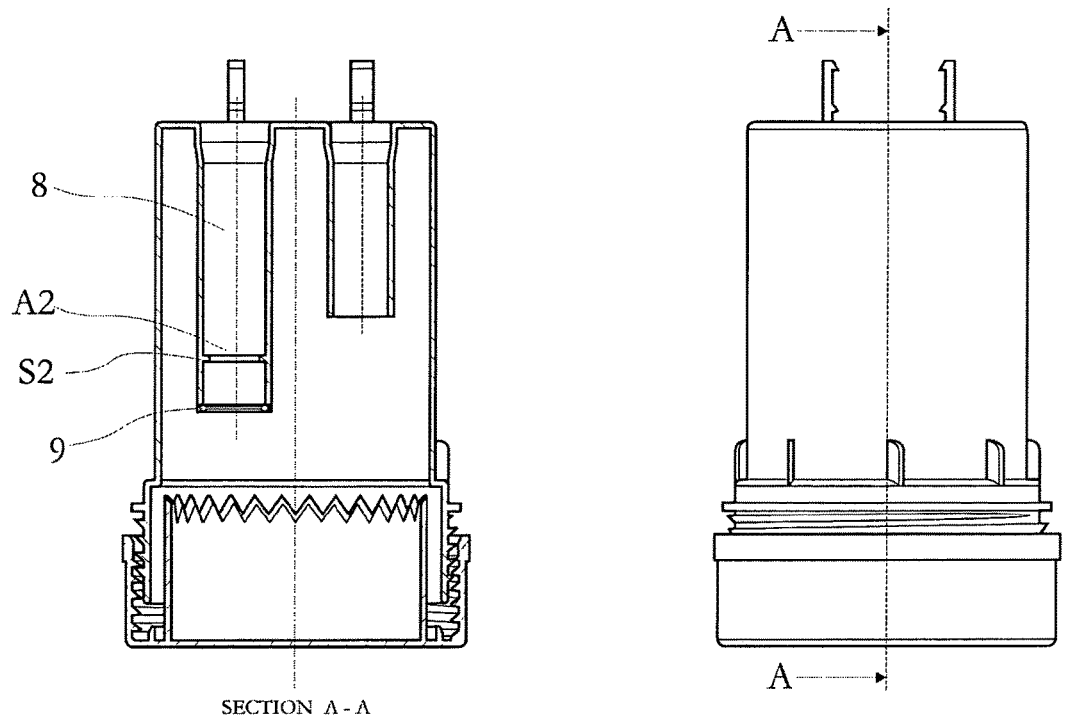
FIG. 3 shows the container (2) provided with a second aperture (A2) in the form of a channel (8) sealed with a second seal (S2), and a mesh (9).
Figure 4:
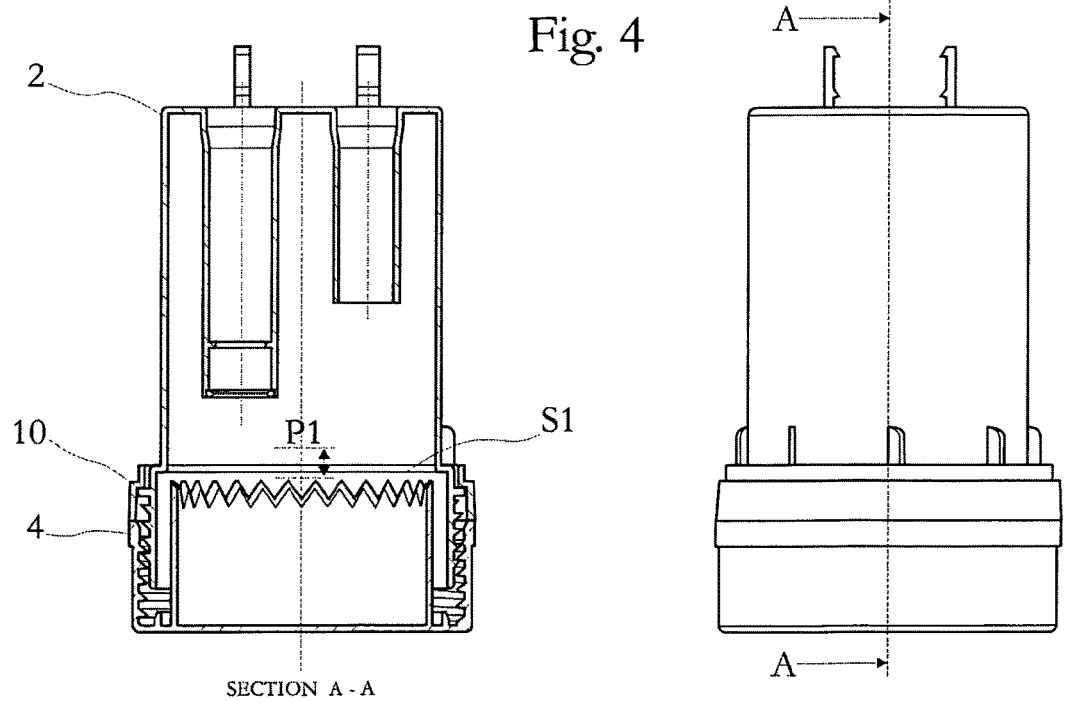
FIG. 4 shows the removable stop means (10) for preventing the lid (4) or the container (2) from reaching the determined position (P1) of the coupling course, therefore avoiding wasting the device (1) by the seal (S1) being broken accidentally before use.
Figure 5:
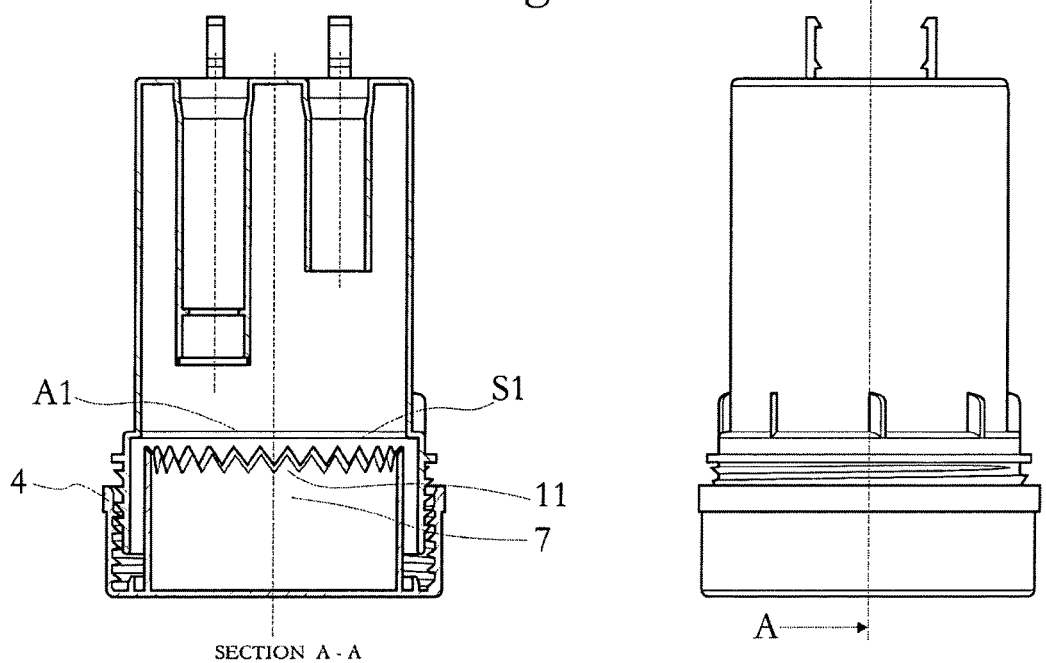
FIG. 5 shows the means (7) for breaking the first seal (S1) of the first aperture (A1) comprise projections (11) on the lid (4) able to tear the first seal (S1)
Figure 5:
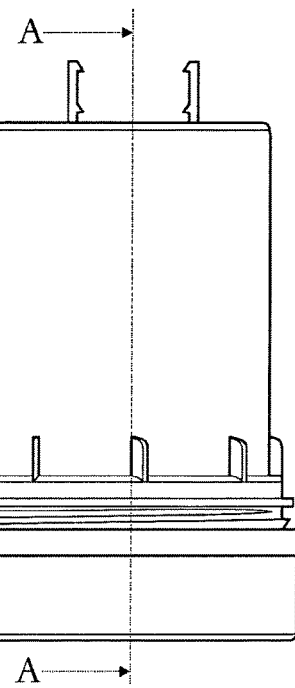
Figure 6:
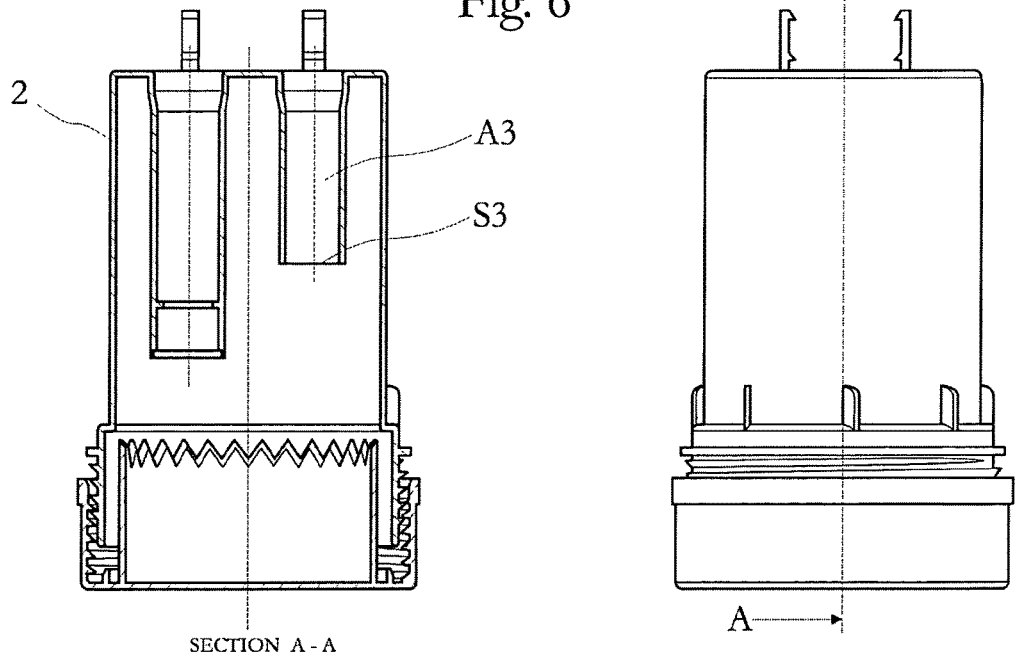
FIG. 6 shows the container (2) further provided with a third aperture (A3) sealed with a third seal (S3).
Figure 6:
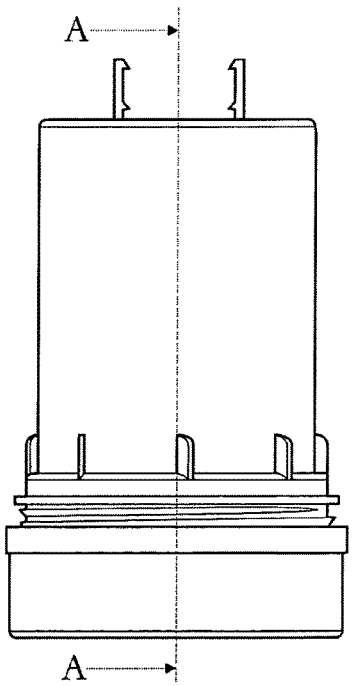

In one embodiment of the present invention, the mesh (9) is located between the second aperture (A2) and the first aperture (A1). In a further embodiment, the mesh (9) is located at the bottom side of the channel (8), i.e. below the second seal (S2), which is placed in an intermediate part of the channel (8), as depicted in FIG. 3.

In one embodiment of the present invention, the device further comprises security means (10) for preventing the lid (4) or the container (2) from reaching the determined position (P1) of the coupling course, said security means (10) being removable, therefore avoiding wasting the device (1) by the seal (S1) being broken accidentally before use.

In one embodiment of the present invention, the security means (10) comprise a security belt placed between the lid (4) and the container (2).

In one embodiment of the present invention, the means (6) for mechanically tight coupling the lid (4) to the container (2) are irreversible when the determined position (P1) of the coupling course between the lid (4) and the container (2) is reached, such that they prevent uncoupling the lid (4) from the container (2), thereby preventing the leakage of the culture medium or test sample (TS) out of the device (1) after the seal (S1) has been broken.

In one embodiment of the present invention, the means (7) for breaking the first seal (S1) of the first aperture (A1) comprise projections (11) on the lid (4) able to tear the first seal (S1).

In one embodiment of the present invention, the container (2) is further provided with a third aperture (A3) sealed with a third seal (S3).

The present invention also relates to a testing injector device (12) configured for accessing the volume (3) of the device (1) for assaying microorganisms or toxins above through the second aperture (A2) of the container (2) by perforating the second seal (S2), said injector device (12) comprising a tube (13) and a slidable plunger (14), wherein the plunger comprises a seal (15) at its bottom (14a) and a lateral flow immunochromatography strip (16) inside along the plunger (14).

This testing injector device (12) has four functions: i) perforator of seal (S2); ii) aspirator of an optionally filtered enriched mixture of sample and culture medium; iii) detector and reader of an immunoassay.

In one embodiment of the present invention, the tube (13) of the injector device (12) comprises extraction medium. In a further embodiment, the extraction medium is placed at the bottom of the tube (13), between the lower end of the tube (13) and the slidable plunger (14).

In one embodiment of the present invention, either the device (1) for assaying microorganisms or toxins, or the injector device (12), comprises security means (17) which when released, allow the injector device (12) to be pushed into the second aperture (A2) and perforate seal (S2).

In one embodiment of the present invention, the security means (17) have the form of a security belt. In a further embodiment, the security means (17) are located around the immediate exterior end of the injector device (12), as depicted in FIG. 8.

In one embodiment of the present invention, either the device (1) for assaying microorganisms or toxins, or the injector device (12), comprises stop means (18) setting a course that allows the plunger (14) of the injector device (12) to aspirate a pre-determined amount of liquid.

In one embodiment, this pre-determined amount of liquid is from 0.1 to 10 mL.

Figure 9:
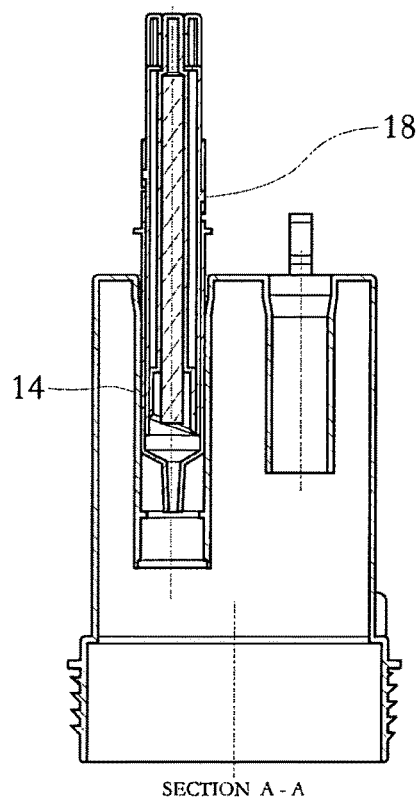
FIG. 9 shows stop means (18) setting a course that allows the plunger (14) of the injector device (12) to aspirate a pre-determined amount of liquid.
Figure 9:
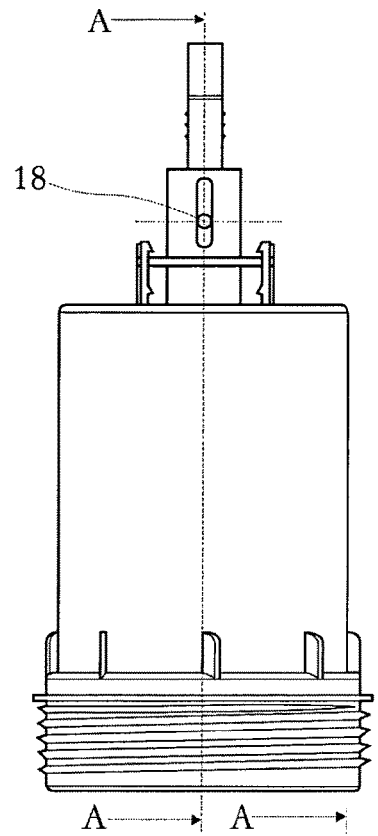

In one embodiment of the present invention, the stop means (18) are located at the injector device (12). In a further embodiment, the stop means (18) are located at the immediate exterior side of the injector device (12) as depicted in FIG. 9. In a further embodiment, the stop means (18) comprise a combination of a longitudinal groove and a protuberance tightly fitting into the groove. In a further embodiment, the longitudinal groove is located at the tube (13) and the protuberance is located at the plunger (14).

In one embodiment of the present invention, either the device (1) for assaying microorganisms or toxins, or the injector device (12), comprises security means (19) which when released allow the immunochromatography strip (16) to be pushed within along the plunger (14) and perforate seal (15).

In one embodiment of the present invention, seal (15) is located at the bottom side of the plunger (14) as depicted in FIG. 7.

In one embodiment of the present invention, the security means (19) are positioned at the top of the plunger (14).

Figure 10:
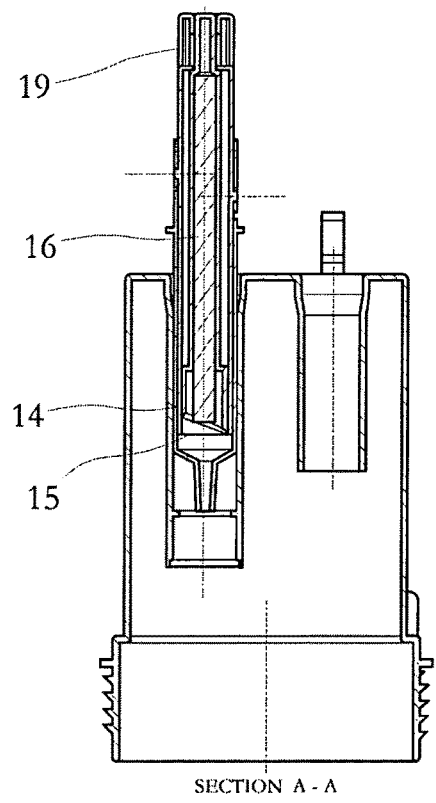
FIG. 10 shows security means (19) which when released, allow the lateral flow immunochromatography strip (16) to be pushed within along the plunger (14) and perforate seal (15)
Figure 10:
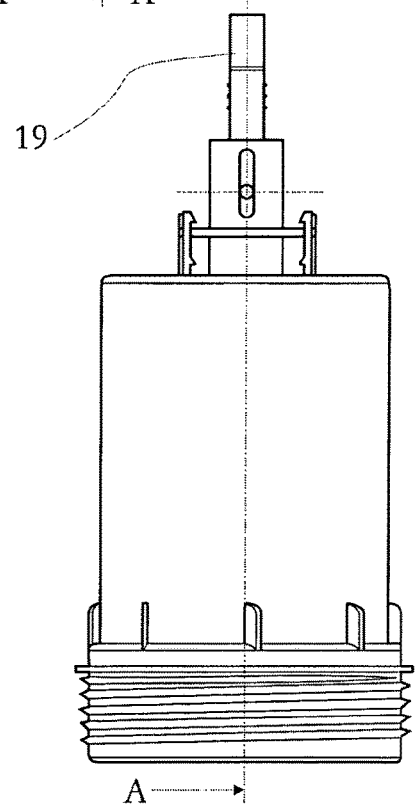
Figure 11:
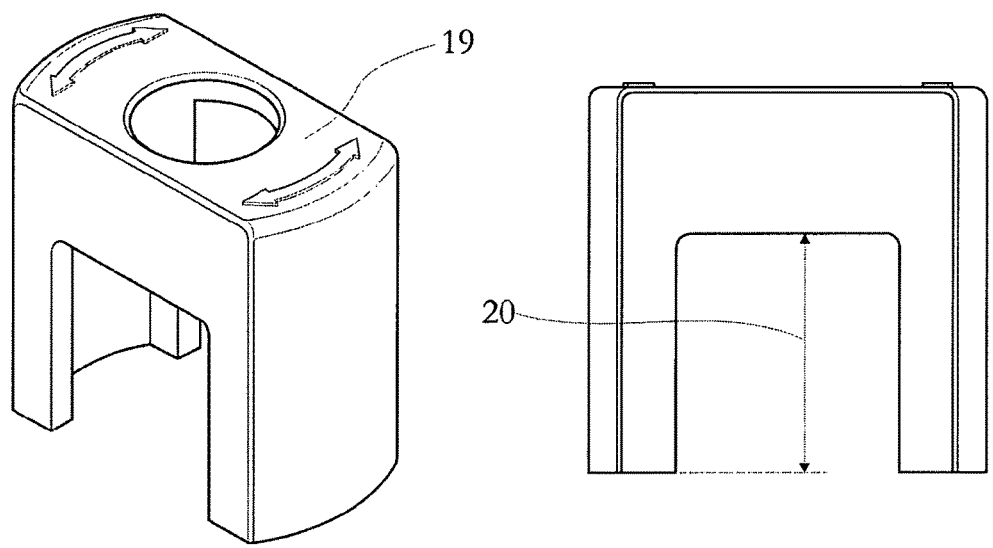
FIG. 11 shows security means (19) in the form of a turnable button. It further shows stop means (20) setting a maximum plunger injecting distance, therefore avoiding wasting the immunochromatography strip.
Figure 12:
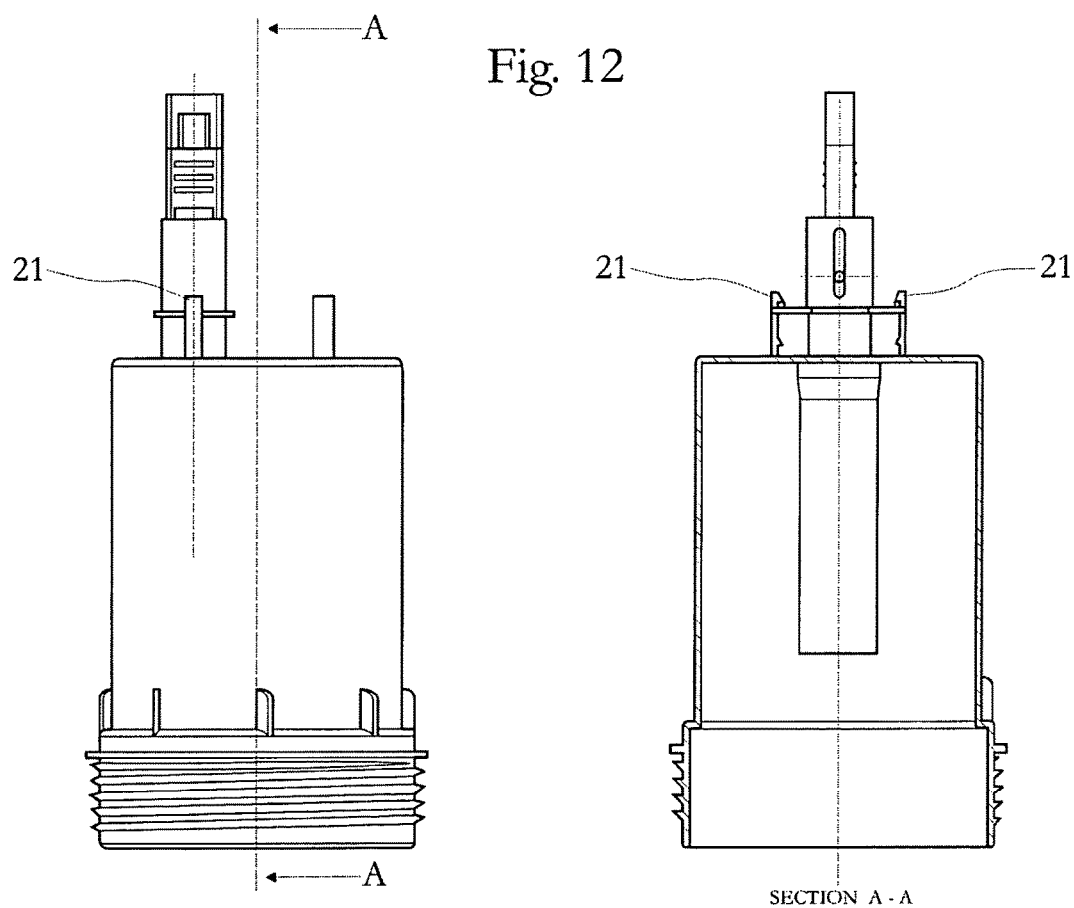
FIG. 12 shows stop means (21) setting a maximum course, therefore avoiding pulling the injector device (12) or any component thereof out from the device (1).
Figure 13:
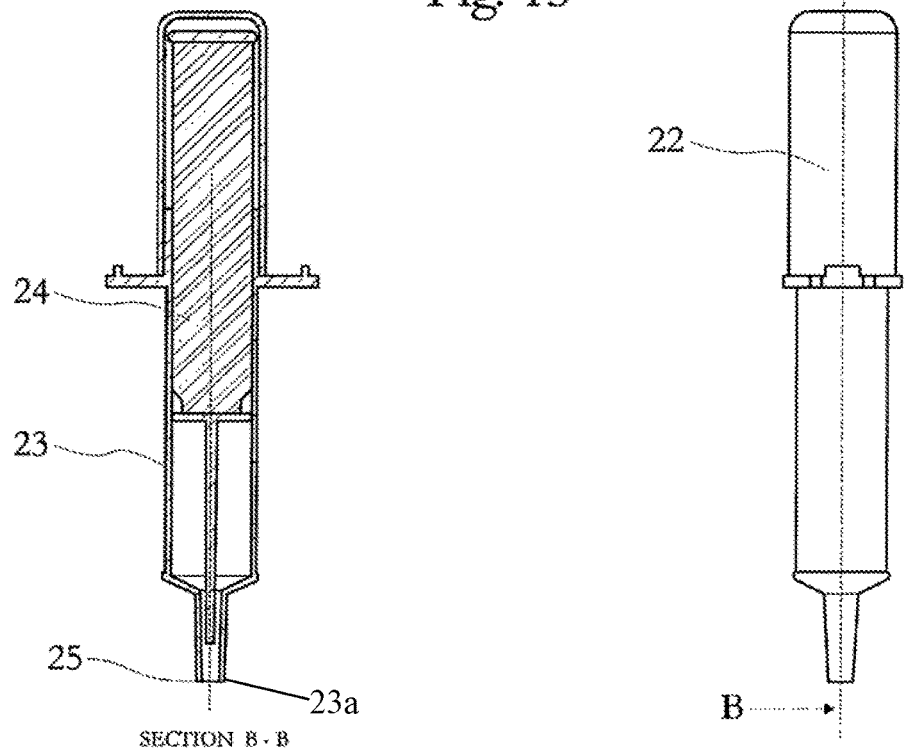
FIG. 13 shows an inactivating injector device (22) comprising a tube (23) and a slidable plunger (24), wherein the tube (23) comprises a seal (25) at its bottom (23a) and the plunger (24) has a sharp end.

In one embodiment, the security means (19) are located at the top of the immunochromatography strip (16), as depicted in FIG. 10. In one embodiment of the present invention, the security means (19) may be released by turning them around as depicted in FIG. 11. In one embodiment, the security means (19) are a security turnable button as depicted in FIG. 11.

In one embodiment of the present invention, either the device (1) for assaying microorganisms or toxins, or the injector device (12), comprises stop means (20) setting a maximum plunger injecting distance, therefore avoiding wasting the immunochromatography strip (16) by contacting said strip with the test sample accidentally before use.

In one embodiment of the present invention, the stop means (20) are located at the device (1). In a further embodiment, the stop means (20) are one or more protuberances or side pieces located around the injector device (12).

In one embodiment of the present invention, either the device (1) for assaying microorganisms or toxins, or the injector device (12), comprises stop means (21) setting a maximum course, therefore avoiding pulling the injector device (12) or any component thereof out from device (1).

In one embodiment of the present invention, the stop means (21) are located at the device (1). In a further embodiment, the stop means (21) are one or more protuberances or side pieces located around the injector device (12).

The present invention further relates to an inactivating injector device (22) configured for accessing the volume (3) of the device (1) through the third aperture (A3) of the container (2) by perforating the third seal (3), said injector device (22) comprising a tube (23) and a slidable plunger (24), wherein the tube comprises a seal (25) at its bottom (23a) and inactivating agent, and the plunger (24) has a sharp end.

In one embodiment of the present invention, either the device (1) for assaying microorganisms or toxins, or the inactivating injector device (22), comprises security means (26) which when released, allow the injector device (22) to be pushed into the third aperture (A3) and perforate seal (S3).

Figure 14:
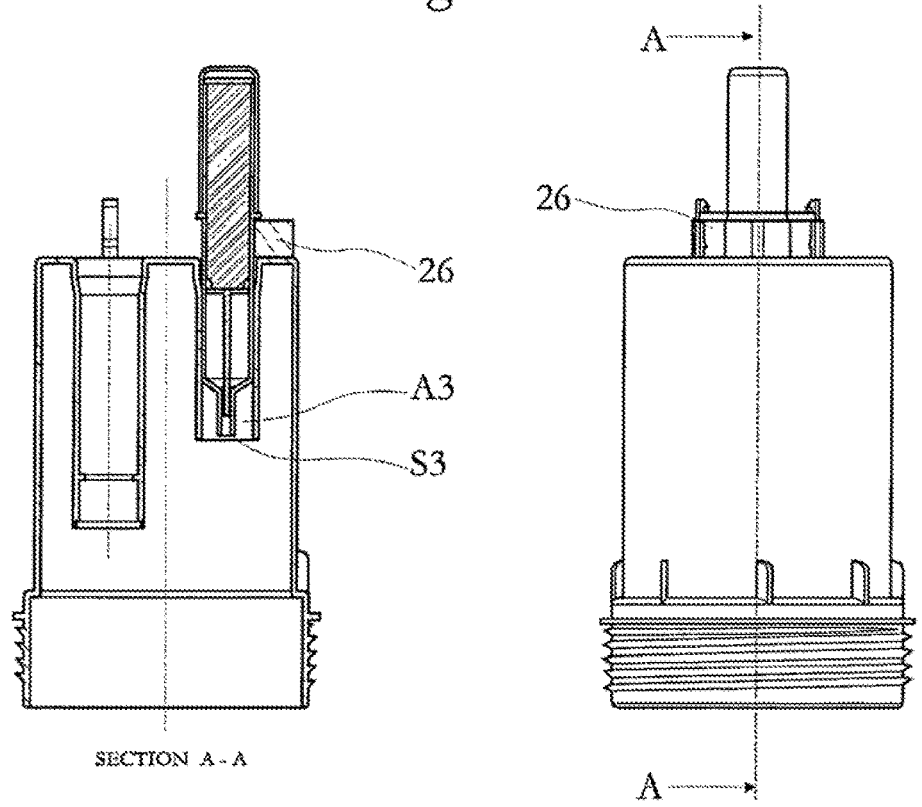
FIG. 14 shows security means (26) which when released allow the injector device (22) to be pushed into the third aperture (A3) and perforate seal (S3).
Figure 15:
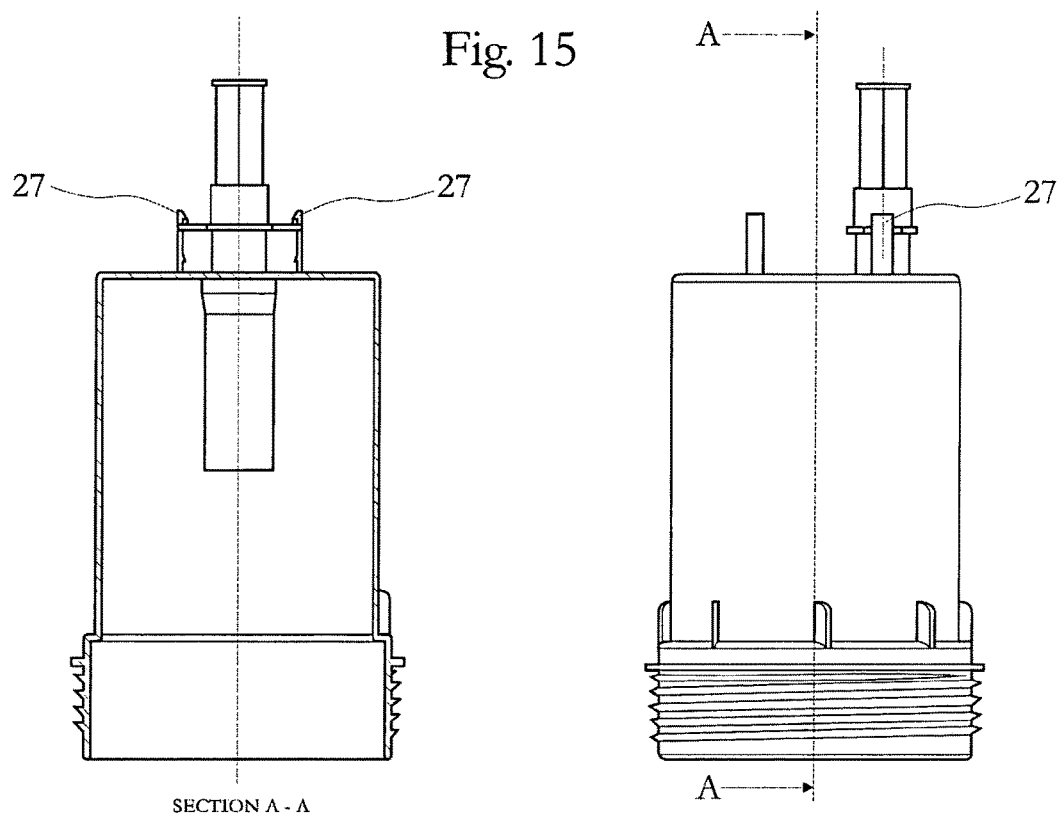
FIG. 15 shows stop means (27) setting a maximum course therefore avoiding pulling the injector device (22) or any component thereof out from the device (1).

In one embodiment of the present invention, the security means (26) have the form of a security belt. In a further embodiment, the security means (26) are located around the immediate exterior part of the inactivating injector device (22), as depicted in FIG. 14.

In one embodiment of the present invention, either the device (1) for assaying microorganisms or toxins, or the inactivating injector device (22), comprises stop means (27) setting a maximum course, therefore avoiding pulling the injector device (22) or any component thereof out from device (1).

In one embodiment of the present invention, the stop means (27) are located at the device (1). In a further embodiment, the stop means (27) are one or more protuberances or side pieces located around the inactivating injector device (22).

Procedure for enriching, aliquoting, or assaying microorganisms or toxins using the devices (1), testing injector device (12), and optionally the inactivating injector device (22)

A test sample (TS) is placed in the housing (5) of the lid (4), which lid (4) is then mechanically tightly coupled to the container (2) with the aid of means (6). While coupling the lid to the container or vice versa, when a determined position is reached (P1), the first seal (S1) becomes broken with the aid of means (7), thereby bringing the culture medium into contact with the test sample. The device (1) becomes closed hermetically and enclosing the test sample and the culture medium, which start to mix.

In one embodiment, the coupling of the lid to the container or vice versa becomes an irreversible action once the determined position of the coupling course is reached, thereby preventing that the lid and the container may be later uncoupled, further preventing the leakage of the culture medium, test sample, and mixture thereof, out of the device after the first seal has been broken.

Once the test sample is placed in the housing of the lid and before reaching position (P1), it is preferable to position the device such that the lid is found on the top side of the device and not at the bottom side (upside down in respect to the position of the device of FIG. 1). With this position, the further coupling of the lid and the container is performed and the breaking of the first seal occurs, preventing like this that any of the interior components leaks out by gravity out of the device.

In one embodiment, the device comprises security means (10), e.g. a security belt, which are removed prior to the coupling of the lid with the container or vice versa. If the security means (10) are present and not removed, the coupling course between the lid and the container does not reach position (P1).

When these security means (10) are removed, the coupling course between the lid and the container may reach position (P1) at which position the first seal (S1) becomes broken, and this action is meant for when the housing of the lid comprises the test sample to be analyzed.

Once the test sample is comprised within the device, and the first seal is broken, the test sample comes into contact with the culture medium. The device (1) is then submitted to suitable incubation conditions for enriching the test sample with the microorganisms or toxins of interest, i.e. those to be detected. In one embodiment, these incubation conditions take from 30 minutes to 48 hours, preferably from 10 to 24 hours, more preferably around 20 hours. In one embodiment, these incubation conditions comprise heating the device (1) at a temperature suitable to enable the growth and enrichment of the mixture with the microorganism or toxin of interest. Suitably, this temperature ranges from 0° C. to 40° C., more suitably between 20° C. and 40° C., even more suitably around 37° C. The heating may be performed in any heating device.

It is known by the skilled in the art that the amount of time and temperature of incubation depends on the type of microorganism or toxin with which the mixture is to be enriched.

In one embodiment of the present invention, the device additionally comprises a mesh (9). In the space between the mesh and the second seal (S2), a fine filtered representation of the culture and sample mixture is confined, being this mixture the one that is further assayed or analyzed.

Next action is to push the testing injector device (12) into the second aperture (A2) by perforating the second seal (S2) of the device (1). Like this, the testing injector device accesses to the interior volume (3) of the container (2).

In one embodiment, prior to pushing the testing injector device (12) into the device (1), security means are released, allowing then the pushing action and perforation of the second seal (S2). These security means may have the form of a security belt for example.

In one embodiment, the device (1) or the injector device (12) comprises stop means that prevent from pushing the injector device too deep into the volume of the container of the device (1) such that the pushed injector device does not perforate the mesh.

In one embodiment, the device (1) or the injector device (12) comprises stop means (20) setting a maximum plunger injecting distance, therefore avoiding wasting the immunochromatography strip by contacting said strip with the test sample accidentally before use.

Once the testing injector device accesses the interior volume of the device, the end part of the testing injector device, preferably a tip, is found in that space between the mesh (9) and the second seal (S2) as depicted in FIG. 3, where a filtered representation of the culture and sample mixture is confined.

The plunger (14) of the injector device is then pulled upwards, aspirating a pre-determined quantity of the filtered culture and sample mixture. In one embodiment, the plunger is pulled as long as the stop means (18) allow. By configuring the stop means (18) at a specific position in the pulling course, the required or pre-determined amount of culture and sample mixture is aliquoted.

In one embodiment, the injector device (12) comprises extraction medium, preferably located at the bottom of the tube (13) near the tip. Thus, when the plunger aspirates the filtered culture and sample mixture, it brings this mixture into contact with the extraction medium.

Preferably, the mixture of test sample, culture medium, and extraction medium is left unmanipulated for a convenient time such that that the analytes of interest can become accessible for their further detection.

Next, the lateral flow immunochromatography strip (16) is pushed downwards within along the plunger (14) perforating seal (15) and therefore coming into contact with the mixture comprising the detectable analytes. This contact is like a dipping action, where the end portion of the strip is impregnated with the analytes solution, which solution starts moving along the strip by capillarity. The analytes in the present invention are the antigenic determinants.

With the special design and configuration of the testing injector device (12) of the present invention, a compartment or chamber is suppressed: the extraction and detection steps are performed in the same chamber.

In one embodiment, security means (19), either located at the device (1) or the injector device (12), must be first released to allow the pushing of the immunochromatography strip downwards within along the plunger (14) and perforate seal (15).

In one embodiment, pulling the injector device (12) or any component thereof out from the device is prevented by the presence of stop means (21) setting a maximum course for the pulling action.

Immunological reaction takes place, whereby the antibodies immobilized onto the immunochromatography bind or not with the relevant antigens from the test sample. The antibodies are tagged or labeled with another molecule which can produce a measurable signal. The signal generated by the tag or label can be a colour change, production of light or fluorescence, an electrical or optical output or by simple visual recognition. In one embodiment, the signal is visually recognizable. In one embodiment, the signal is quantifiable.

In one embodiment, the reading of the result takes place through a visor located at the exterior of the injector device. The visor is a transparent section of the injector device showing the signals, preferably the typical detection and control bands of immunochromatography strips.

In one embodiment, once the detection and reading steps have taken place, the mixture of test sample, culture medium, optionally extraction medium may be pushed downwards to the interior volume (3) of the device (1) so that this aliquot is confined therein, or alternatively is further inactivated.

In one embodiment, the container (2) of the device (1) is further provided with a third aperture (A3) sealed with a third seal (S3).

In this device (1) configuration, the inactivating injector device (22), configured for accessing the volume (3) of the device (1), is then pushed through the third aperture perforating the third seal. During this pushing action, the plunger (24) is pushed simultaneously within the tube (23) thereby perforating seal (25) located at the bottom (23a) of the tube. Like this, the inactivating agent is put in contact with the enriched mixture, thereby inactivating said mixture. The inactivating injector device (22) and device (1) are both made of a material resistant to the inactivating agent.

It should be noted that seal (25) is useful in keeping the inactivating agent confined within the inactivating injector device (22) without leaking out of said device (22). This seal (25) is preferably useful when the inactivating agent is in liquid state.

In one embodiment, this pushing and perforating action of the inactivating injector device (22) is only possible when the security means (26) are released.

In one embodiment, would the manipulator desire to pull out the inactivating injector device (22) or any components thereof out of the device (1), the device (1) is also provided with stop means (27) setting a maximum course that impedes this action.

The present invention also relates to a method for enriching microorganisms or toxins comprising: placing a test sample (TS) into the housing (5) of a lid (4) of a device (1) ;

mechanically tight coupling the lid (4) to a container (2) of the same device (1), wherein the container encloses a volume (3) filled with a culture medium for a microorganism and provided with a first aperture (A1) sealed with a first seal (S1) and a second aperture (A2) sealed with a second seal (S2); and breaking the first seal (S1) by reaching a determined position (P1) of the coupling course between the lid (4) and the container (2), thereby bringing the culture medium into contact with the test sample;

submitting said device (1) to suitable incubation conditions.

The present invention further relates to a method for aliquoting microorganisms or toxins comprising:

placing a test sample (TS) into the housing (5) of a lid (4) of a device (1);

mechanically tight coupling the lid (4) to a container (2) of the same device (1), wherein the container encloses a volume (3) filled with a culture medium for a microorganism and provided with a first aperture (A1) sealed with a first seal (S1) and a second aperture (A2) sealed with a second seal (S2); and breaking the first seal (S1) by reaching a determined position (P1) of the coupling course between the lid (4) and the container (2), thereby bringing the culture medium into contact with the test sample; submitting said device (1) to suitable incubation conditions;

pushing a syringe into the second aperture (A2), breaking the second seal (S2), and extracting a pre-determined amount of test sample.

The present invention further relates to a method for assaying microorganisms or toxins comprising:

placing a test sample (TS) into the housing (5) of a lid (4) of a device (1);

mechanically tight coupling the lid (4) to a container (2) of the same device (1), wherein the container encloses a volume (3) filled with a culture medium for a microorganism and provided with a first aperture (A1) sealed with a first seal (S1) and a second aperture (A2) sealed with a second seal (S2), and wherein the container (2) is optionally provided with a third aperture (A3) sealed with a third seal (S3); and breaking the first seal (S1) by reaching a determined position (P1) of the coupling course between the lid (4) and the container (2), thereby bringing the culture medium into contact with the test sample;

submitting said device (1) to suitable incubation conditions;

pushing a testing injector device (12) into the second aperture (A2), thereby breaking the second seal (S2), wherein the testing injector device (12) is configured for accessing the volume (3) of the device (1) according to the present invention through the second aperture (A2) of the container (2) by perforating the second seal (S2), said injector device (12) comprising a tube (13) and a slidable plunger (14), wherein the plunger comprises a seal (15) at its bottom (14a) and a lateral flow immunochromatography strip (16) inside along the plunger (14);

aspirating a pre-determined amount of test sample (TS) by pulling the plunger (14); and pushing the lateral flow immunochromatography band (16) and breaking the seal (15) at the bottom (14a) of the plunger;

reading the results;

optionally pushing an inactivating injector device (22), thereby inactivating the interior components of the device (1), wherein the inactivating injector device (22) is configured for accessing the volume (3) of the device (1) according to the present invention through the third aperture (A3) of the container (2) by perforating the third seal (3), said injector device (22) comprising a tube (23) and a slidable plunger (24), wherein the tube comprises a seal (25) at its bottom (23a) and inactivating agent, and the plunger (24) has a sharp end.

In one embodiment, in any one of the methods for enriching, aliquoting, or assaying microorganisms or toxins, the container (2) is further provided with a mesh (9) on the volume side with respect to said second seal (S2).

In one embodiment, in the method for aliquoting microorganisms or toxins, the syringe is the testing injector device (12).

In one embodiment, in any one of the methods for enriching, aliquoting, or assaying microorganisms or toxins, the device (1) further comprises security means (10) for preventing the lid (4) or the container (2) from reaching the determined position (P1) of the coupling course, said security means (10) being removable, therefore avoiding wasting the device (1) by the seal (S1) being broken accidentally before use.

In one embodiment, in any one of the methods for enriching, aliquoting, or assaying microorganisms or toxins, the means (6) for mechanically tight coupling the lid (4) to the container (2) are irreversible when the determined position (P1) of the coupling course between the lid (4) and the container (2) is reached, such that they prevent uncoupling the lid (4) from the container (2), thereby preventing the leakage of the culture medium or test sample (TS) out of the device (1) after the seal (S1) has been broken.

In one embodiment, in any one of the methods for enriching, aliquoting, or assaying microorganisms or toxins, the means (7) for breaking the first seal (S1) of the first aperture (A1) comprise projections (11) on the lid (4) able to tear the first seal (Si).

In one embodiment, in any one of the methods for aliquoting, or assaying microorganisms or toxins, the tube (13) of the injector device (12) comprises extraction medium.

In one embodiment, in any one of the methods for aliquoting, or assaying microorganisms or toxins, either device (1) or (12) comprises security means (17) which when released, allow the injector device (12) to be pushed into the second aperture (A2) and perforate seal (S2).

In one embodiment, in any one of the methods for aliquoting, or assaying microorganisms or toxins, either device (1) or (12) comprises stop means (18) setting a course that allows the plunger (14) of the injector device (12) to aspirate a pre-determined amount of liquid.

In one embodiment, in any one of the methods for aliquoting, or assaying microorganisms or toxins, either device (1) or (12) comprises security means (19) which when released, allow the immunochromatography strip (16) to be pushed within along the plunger (14) and perforate seal (15).

In one embodiment, in any one of the methods for aliquoting, or assaying microorganisms or toxins, the security means (19) are positioned at the top of the plunger (14).

In one embodiment, in any one of the methods for aliquoting, or assaying microorganisms or toxins, either device (1) or (12) comprises stop means (20) setting a maximum plunger injecting distance, therefore avoiding wasting the immunochromatography strip (16) by contacting said strip with the test sample accidentally before use.

In one embodiment, in any one of the methods for aliquoting, or assaying microorganisms or toxins, either device (1) or (12) comprises stop means (21) setting a maximum course, therefore avoiding pulling the injector device (12) or any component thereof out from device (1).

In one embodiment, in any one of the methods for aliquoting, or assaying microorganisms or toxins, either device (1) or (22) comprises security means (26) which when released, allow the injector device (22) to be pushed into the third aperture (A3) and perforate seal (S3).

In one embodiment, in any one of the methods for aliquoting, or assaying microorganisms or toxins, either device (1) or (22) comprises stop means (27) setting a maximum course, therefore avoiding pulling the injector device (22) or any component thereof out from device (1).

Industrial Applications of the Devices

The devices (1), (12), or (22) according to the present invention, in any one of the embodiments presented herein are useful as detectors of environmental or food contamination. As such the present invention relates to the devices (1), (12), or (22) for use as a detector of environmental or food contamination.

The device (1) according to the present invention, in any one of the embodiments presented herein is also useful as an enricher or aliquoter of test samples. As such the present invention relates to the device (1) for use as an enricher or aliquoter of test samples.

Aliquoting of enriched test samples can be performed by perforating the second seal and extracting the pre-determined amount of filtered enriched test sample mixture. Such action may be performed with a typical syringe that can perforate the second seal and aspirate the pre-determined volume. In one embodiment, the device (1) comprises stop menas setting a course that allows the plunger of a typical needle to aspirate a pre-determined amount of volume.

For each type of microorganism or toxin, a specific testing injector device (12) with an appropriate immunochromatography strip and extraction medium is selected, as well as a specific device (1) with a convenient culture medium for selecting and enriching the test sample with the microorganism to be detected. Optionally, the inactivating injector device (22) may be customized for the microorganisms to be inactivated.

In summary, the inventive device offers the possibility to detect qualitatively biological hazard agents complying with the regulations without the need for installations or skilled personal. The state of the art devices are based on a surface sampling but that does not allow to enrich completely a macro-sample, which has to be understood as a sample of a few grams.

This new device allows detecting the presence/absence of biological hazard agents in 25 g/25 ml of aliment, specially thanks to the visual indicator incorporated in the second housing. The devices described in U.S. Pat. No. 6,197,574, WO97/03209A1, FR 2849861 A1, US 2009 0197283 A1 and EP 1712614 does not allow the enrichment and testing of macrosamples.

More specifically, the device of the invention will allow the small companies to fulfil the CE regulation No. 2073/2005-15 Nov. 2005, which establish the microbiological criteria applicable to the aliments, including the qualitative control of pathogens in the factory and in the final product.

What is claimed is:

1. A portable device for detecting biological hazard agents in a solid macrosample comprising:
a container comprising an external surface provided with an outer thread, the container enclosing a first housing filled with a culture medium for biological hazard agents,
a second housing for receiving the solid macrosample,
a lid comprising an outer perimeter wall provided with an inner thread, said inner thread being complementary to the outer thread of the external surface of the container, so that the lid is adapted to be coupled by screwing along a coupling course to the container,
a tearable first seal that separates the first housing and the second housing and that, when teared, communicates the first housing and the second housing such that the culture medium for biological hazard agents and the solid macrosample are brought into contact and mix with each other to obtain an enriched test sample mixture from the solid macrosample,
a confined receptacle located within the container and communicates with the first housing or with the second housing through a filter or mesh to receive a predetermined fine filtered portion of the enriched test sample mixture therefrom,
an immunochromatography strip enclosed within a third housing for sensing a presence of biological hazard agents in a predetermined aliquot of the predetermined fine filtered portion of the enriched test sample mixture, and
said third housing being provided with a transparent surface that allows the immunochromatography strip to be seen from the outside, wherein the third housing is adapted to access said confined receptacle through an aperture sealed with a tearable second seal formed in between the confined receptacle and the third housing to extract said predetermined aliquot of the predetermined fine filtered portion of the enriched test sample mixture therefrom, to be accessed by the immunochromatography strip,
wherein the second housing has an inlet surface greater than 10 $cm^2$ and comprises at least one visual indicator corresponding to a predetermined filling volume,
wherein the second housing is in the lid, wherein the lid is a plate,
wherein the lid further comprises an inner perimeter wall arranged within the outer perimeter wall, the inner perimeter wall enclosing the second housing and having a brim and a plurality of cutting elements distributed on the brim, the plurality of cutting elements being configured to tear the tearable first seal along a circumferential path when the lid is screwed to the container from a first determined coupling position to reach a determined second coupling position along the coupling course.

2. The portable device according to claim 1, wherein the first housing has a volume between about 50 ml and about 500 ml, and wherein the second housing has a volume between about 5 ml and about 300 ml.

3. The portable device according to claim 1, wherein the portable device further comprises inertizing means enclosed in a fourth housing.

4. The portable device according to claim 3, wherein the fourth housing containing the inertizing means is arranged in the lid.

5. The portable device according to claim 4, wherein the inertizing means is solid.

6. The portable device according to claim 1, wherein the portable device comprises a security element to prevent at least one of the lid or the container from reaching the first determined coupling position along the coupling course, wherein said security element comprises a removable security belt arranged between the lid and the container.

7. The portable device according to claim 1, wherein said tearable second seal separates the third housing from the first housing and that delimits, together with said mesh or filter, said confined receptacle, the third housing within the container including a testing module configured to extract said predetermined aliquot from the confined receptacle by breaking the tearable second seal, wherein the testing module includes an injector comprising a tube and a plunger slidably coupled to the tube, and wherein the immunochromatography strip is arranged inside the tube and affixed to the plunger.

\* \* \* \* \*